(12) United States Patent
Goorden et al.

(10) Patent No.: US 6,538,157 B1
(45) Date of Patent: Mar. 25, 2003

(54) METHOD FOR THE PREPARATION OF UREA

(75) Inventors: Josephus Johannes Petrus Maria Goorden, Roosendaal (NL); Jacobus Johannes De Wit, Amstelveen (NL)

(73) Assignee: Continental Engineering B.V., Amsterdam (NL)

( * ) Notice: Subject to any disclaimer, the term of this patent is extended or adjusted under 35 U.S.C. 154(b) by 0 days.

(21) Appl. No.: 10/030,551

(22) PCT Filed: Jul. 12, 2000

(86) PCT No.: PCT/NL00/00492

§ 371 (c)(1),
(2), (4) Date: Jun. 12, 2002

(87) PCT Pub. No.: WO01/04085

PCT Pub. Date: Jan. 18, 2001

(30) Foreign Application Priority Data

Jul. 12, 1999 (NL) .............................................. 1012575

(51) Int. Cl.$^7$ ............................................. C07C 273/04
(52) U.S. Cl. .............................. 564/70; 564/66; 564/67
(58) Field of Search .............................. 564/66, 67, 70

(56) References Cited

FOREIGN PATENT DOCUMENTS

WO  wo 89/01468  2/1989

*Primary Examiner*—Peter O'Sullivan
(74) *Attorney, Agent, or Firm*—Young & Thompson

(57) ABSTRACT

A method for the preparation of urea in a reactor using ammonia and carbon dioxide as starting materials, includes a) bringing the ammonia and carbon dioxide into contact in the reactor under conditions for the formation of carbamate; and b) decomposing the carbamate thus formed to give urea and water. The water formed during step b) is removed from the reaction mixture by a water-selective membrane which is preferably a pervaporation membrane, such as a porous ceramic membrane. Furthermore, a pressure difference is preferably maintained or applied over the selective membrane. The method can in particular be carried out in liquid circulating stream which, in addition to the reactants fed to the circulating stream and the carbamate formed in step a), also contains at least some of the water formed in step b) and also the urea formed in step b), the urea being recovered from the circulating stream and the circulating stream being recycled to the reactor.

9 Claims, 2 Drawing Sheets

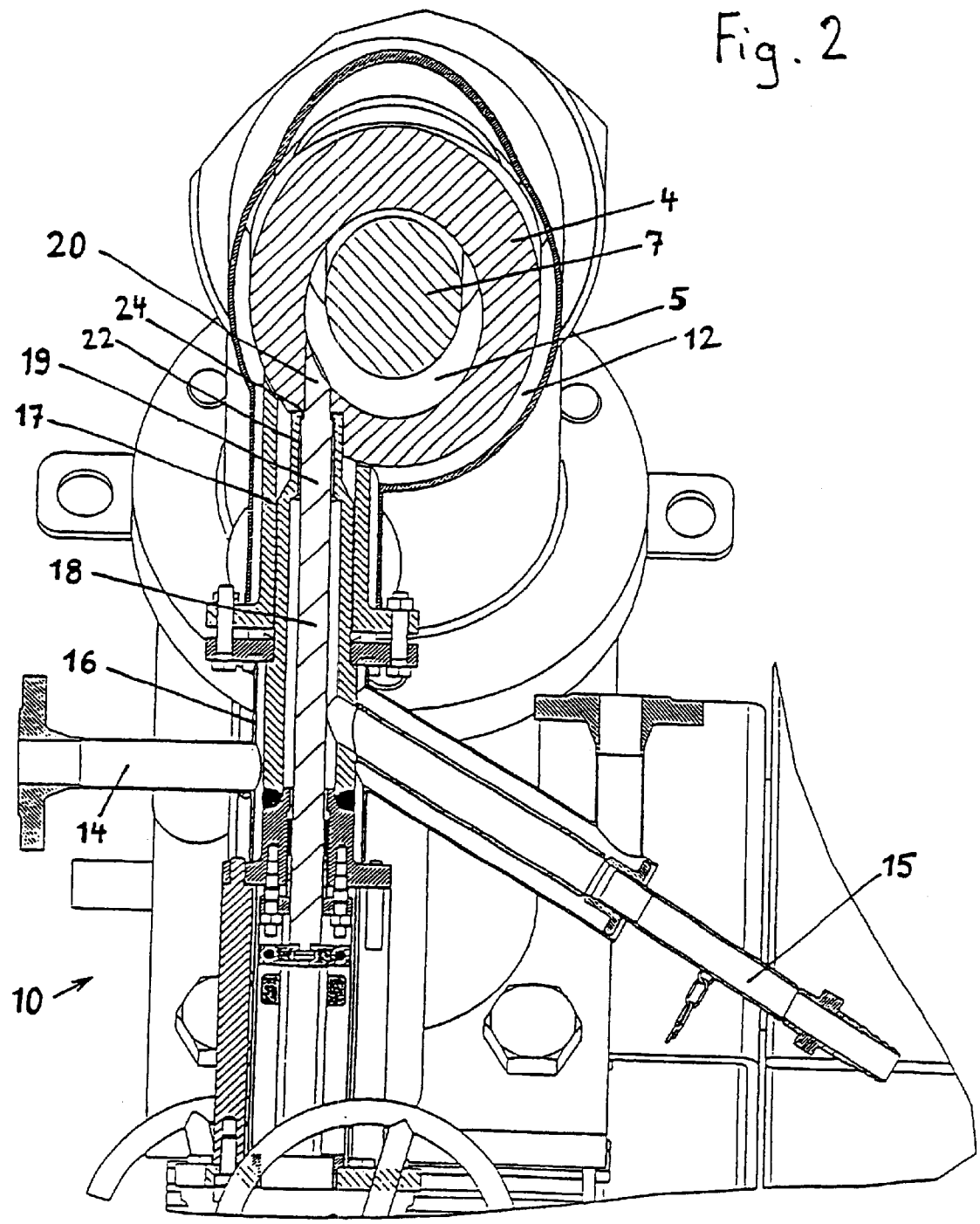

METHOD FOR THE PREPARATION OF UREA

This application is a 371 of PCT/NL00/00492 filed Jul. 12, 2000.

BACKGROUND OF THE INVENTION commercial urea processes consist overall of three process steps, that is to say synthesis; prilling, granulation or crystallisation; and effluent treatment and circuits for recycling carbamate to the reactor.

The synthesis step usually comprises two half-)reactions i.e.:

1) Reaction of ammonia with carbon dioxide, which reaction proceeds rapidly and completely to give carbamate in accordance with the reaction equation:

$$2NH_3 + CO_2 \rightarrow NH_2CO_2NH_4$$

2) The reaction for the dehydration of carbamate to give urea in accordance with the equation $$NH_2CO_2NH_4 \leftrightarrows (NH_2)_2O + H_2O$$

The latter reaction is an equilibrium reaction and in the usual urea processes achieves approximately 50–60% conversion. The carbamate reaction is highly exothermic and the urea reaction is endothermic.

In modern processes the major proportion of the unconverted carbamate is decomposed in a steam stripper and, via a condensation step in which steam is recovered, is recycled to the reactor. The economy of these known processes is highly linked to the yield from the urea synthesis reaction because the latter to a large extent determines how large the recirculation steams are.

In the 1960s and 70s substantial progress was made in the economy of conventional urea processes by installing a high pressure stripper in the urea process. With this arrangement, in this stripper a substantial proportion of the unconverted carbamate in the reactor discharge is recycled, with a limited water content, via a high pressure condensation step directly to the reactor with the feed ($CO_2$ or $NH_3$) to the urea process.

The most important developments for further improvement of the yield in the urea process the 1980s and 90s can be summarised in the following modifications to the reactor section:

produce more plug flow in the reactor
combination of the urea reactor with other process steps
allow the reaction to take place in temperature zones
install a second reactor
remove water via condensation of gas between the reactors.

In Netherlands Patent 1 000 416 the condensation step by means of which the high-pressure recycle stream is usually recycled to the reactor is combined with the reactor. With this arrangement the reactor is oriented horizontally. The $NH_3$ is fed into the cooled section of the reactor. The gas from the stripper is distributed transversely to the liquid stream in the reactor. The intention is that as much urea as possible should already be formed in the cooled section of the reactor. Furthermore, the urea equilibrium in the reactor is better approached by fitting baffles. These prevent backmixing and give a better approach to plug flow than the screen plates in a conventional vertical reactor, as a result of which the synthesis reaction proceeds more rapidly.

EP 0 751 121A2 presents a process in which the urea reaction is distributed over two temperature zones. One of the zones is at relatively low temperature, as a result of which the carbamate equilibrium shifts to higher values, and the other temperature zone is at relatively high temperature, as a result of which the urea equilibrium shifts to higher value. Between the zones water is also separated off by condensation.

EP 0 727 414A1 a process is employed which has an additional reactor under high pressure and temperature in order to achieve a higher conversion.

In EP 0 624 571 A1 a urea process with high yield is described which has an additional reactor, water being removed from the feed to the second reactor by means of condensation. A separate feed control to this reactor makes it possible to maintain an optimum temperature and $NH_3/CO_2$ ratio.

The process improvements in the urea process have to date been directed towards achieving an equilibrium for conversion to urea that is as advantageous as possible and approaching this as closely as possible by, within the limitations which apply for this high pressure and temperature process, feeding a minimum amount of water to the reactor (s) and optionally carrying out interim water removal between two reactors, choosing the process conditions pressure, temperature and residence time to be as optimum as possible, choosing a high $NH_3$ concentration and as far as possible approaching a plug flow regime in the reactor.

However, during the reaction for the formation of urea a quantity of water which is equimolar to the urea produced is formed at the same time. This substantial quantity of water formed still always ensures that the equilibrium for conversion to urea in the reaction is 20–30% below the maximum conversion of 100%.

SUMMARY OF THE INVENTION

The aim of the present invention to improve the known processes and the invention relates in particular to the removal of water from the urea reactor during the synthesis in order to improve the yield. Specifically, by removing water the equilibrium of the reaction for the formation of urea is shifted towards more extensive conversion to urea.

The removal of this quantity of water formed during the reaction, in order substantially to increase the conversion to urea in the urea process reactor and to reduce the recycle streams, has to date not proved possible in practice. This is a consequence of the high degree of difficulty associated with such a water separation step. An adequate selective water separation step was a technology which did not yet exist for the very high pressure ad temperature conditions in the urea process and the reactor environment, which is highly aggressive from the corrosive standpoint.

According to the invention a water-selective membrane, in particular a pervaporation membrane, is now used to remove the water formed during the formation of urea-that is to say during the abovementioned reaction step 2)—from the reactor, optionally in combination with a pressure drop over said membrane.

In first aspect the invention therefore relates to a method for the preparation of urea in a reactor using ammonia and carbon dioxide as starting materials, which method comprises;

a) bringing the ammonia and carbon dioxide into contact in the reactor under conditions for the formation of carbamate; and b) dehydrating the carbamate thus formed to give urea and water, characterised in that the water formed during step b) is removed from the reaction mixture by the us of a water-selective membrane.

To this end the reaction mixture (or at least the reaction mixture in step b)) is brought into contact in the reactor with one side of the selective membrane, the water formed during step b) being removed from the reaction mixture trough said membrane to the other side of the membrane, where it is caught/collected and from where it is removed formed the reactor. During this operation a pressure difference is preferably maintained or applied over the membrane.

The reaction is preferably carried out in the liquid phase, that is to say the reactants (in particular ammonia and carbon dioxide in step a) and carbamate in step b)) are mainly, and preferably essentially exclusively, in the liquid phase.

As a rule the reaction will be carried out as if in a cyclic process. With is arrangement said cyclic process can comprise a high-pressure cycle and a low-pressure cycle is described in more detail below. (A possible advantage of the invention could be that the high-pressure cycle can optionally be omitted, as explained in more detail below), The invention can—with suitable modifications of the equipment used (reactor)—be employed with virtually all known urea processes, including the Stamicarbon processes. Reference is made to the known handbooks, such as the "Encyclopedia of Chemical Technology", Ed. Kirk-Othmer, Wiley Interscience, $3^{rd}$ Ed (1983), vol. 23, pages 515–561, for descriptions of these known urea processes.

According to one embodiment (the carbon dioxide stripping process), the carbon dioxide is fed via a stripper and carbamate condenser to the reactor. The ammonia is fed together with the low-pressure recycle via the condenser to the reactor.

According to another embodiment (using a so-called pool reactor), the ammonia and the carbon dioxide are fed (via the stripper) to said aqueous liquid stream on entering the reactor after which the mixture is fed through the reactor, whereby urea is formed.

In both embodiments the product stream thus obtained is then removed from the reactor ad fed to a stripper, where the carbon dioxide and ammonia still present are removed. The latter are then recycled as a gaseous stream to the reactor (the "high-pressure cycle") This can possibly also still contain residues of carbamate and/or water. (In the conventional processes a carbamate condenser is optionally used in the high-pressure cycle; in the case of a pool reactor this carbamate condenser is integrated in the reactor.) liquid stream which contains water, the—now concentrated—urea and any residues of carbamate still present is also obtained from the stripper. The urea is recovered from this stream by means of working-up steps known per se, after which the residual stream is recycle to the reactor (the "low-pressure cycle").

The selective membrane used according to the invention is at least permeable to water and preferably essentially impermeable to other constituents of the reaction mixture. In particular membranes such as are used in so-called "pervaporation" processes, such as, for example, polymer (organic) membranes or ceramic membranes, which can be non-porous, can be used for this purpose. Reference is made to the known handbooks, such as Perry's Chemical Engineers Handbook, $7^{th}$ Ed. McGraw-Hill, 1997, Section 22–67 to 22–69, for a more detailed description of such "pervaporation membranes".

Preferably a porous ceramic membrane is used, that is to say a membrane having a suitable pore size and thickness, which will be apparent to those skilled in the art. Pore sizes in range from 0.5 nanometre to 1 micrometre and a membrane thickness in the range 1 to 5 mm are preferred.

Examples of suitable membranes are ceramic membranes made of, for example, silica or silica/alumina; silicalite (HZSM5); silicalite/ZSM 5 zeolite; zeolite A/X (e.g. A4/A5, X13) and palladium-containing ceramic materials; and also carbon membranes and membranes made of sintered stainless steel Such membrane materials can have been further modified in a manner known per se, for example by means of ion exchange (for example sodium for copper, etc.), by means of surface treatment and the like. Examples of these and other suitable membranes will be apparent to those skilled in the art, with regard to which reference is again made to the description of pervaporation processes in the known handbooks.

The membranes are preferably suitable for use at the operating temperature for the process ad against any pressure drop applied over the membrane and also against the constituents of the reaction mixture.

It is found that adequate selective removal of water during the urea synthesis in the reactor be achieved by the use of these membranes, integrated in the urea reactor in an adequate manner. The major difficulties which existed for performing selective water removal in situ during the urea reaction are solved by means of this method and process design. By employing this method and process design it is possible to increase the conversion to urea per reactor pass by 10–20%.

The membrane can be of any suitable shape and size and can, for example, be a flat membrane a spirally wound membrane, a "plate and frame" module or a hollow fibre membrane. In this context the membrane is preferably so constructed that it defines, at at least one side thereof, a discharge chamber or discharge channel that is essentially closed off (from reaction chamber), that is to say on its own, in combination with one or more other membranes present and/or in combination with other elements of the reactor, such as the wall(s of the reactor or baffles, plates or trays present in the reactor. During operation of the reactor one side of the membrane is in contact with the reaction mixture, whilst that side of the membrane which forms the discharge channel or the discharge chamber is effectively connected to a discharge line, by means of which the water removed from the reaction mixture can be discharged from the reactor.

The Factor can be provided with a single membrane module (i.e. membrane and discharge ine/discharge chamber) or with multiple modules, which optionally can be connected or joined to one another. The total surface area of the membranes will depend on the size of the reactor and the conversion to be achieved. According to a preferred embodiments the reactor is divided into two or more segments by one or more baffles, plates or trays provided in the rector, each segment optionally being provided with its own member module, the reactants essentially being supplied at one end of the reactor, after which the reaction mixture runs through the various segments in the reactor and is then removed from the reactor at the other end. This prevents back-mixing and promotes the formation of a plug flow. With this arrangement the reactor can be positioned either essentially horizontally or essentially vertically; furthermore a temperature gradient can be maintained or applied over the segments of the reactor.

The design of the reactor, and in particular the positioning of the membranes, baffles, trays and walls, is furthermore preferably such that the rising gas in the urea reactor gives rise to turbulent flow in the reactor during operation, in particular at the membrane surface on the reactor side.

Since the reaction is preferably carried out at elevated temperature—usually in the range from 150–250° C.—and elevated pressure—usually in the range from 100 to 200 bar —the reactor is preferably constructed as an essentially sealed pressure vessel provided with the one or more membrane units and suitable feed and discharge lines. The reactor can furthermore contain all elements of urea reactors that are known per se, such as heating element, mixing and stirring units, cooling elements, measurement and control equipment and the like.

Suitable reactor designs will be apparent to those skilled in the art. In practice it will be possible to make use of a reactor known per se for the synthesis of urea which is provided with one or more membrane modules in accordance with the invention.

During operation water is withdrawn from the reaction zone through the membranes until the desired conversion has been reached, and preferably essentially continuously. To this end pressure difference is preferably applied over the membrane—for example with a pressure drop in the range of 50–200 bar—with the high(er) pressure on the reaction mixture side. To this end the discharge side of the membrane can be effectively connected to a vacuum pump, optionally in combination with a cooler.

The quantity of water which is removed from the reactor during the reaction is preferably such that the carbamate decomposition step in the outlet from the urea reactor offers no further advantages and the $CO_2$, feed gas can be fed directly to the reactor, omitting this carbamate decomposition step. This means that the abovementioned reaction steps a) and b) can essentially be carried out in a single reactor.

The temperature of the reactor, and in particular the beat required for the pervaporation, is preferably essentially obtained/maintained by the carbamate reaction of feed components to, the reactor and/or by condensation of the stripping gas supplied.

BRIEF DESCRIPTION OF THE DRAWINGS

The invention will now be explained on the basis of the following description and the non-limiting FIGS. 1 and 2, which show preferred embodiment of the urea reactor according to the invention—with selective membranes for the removal of water. More particularly:

FIG. 2 shows a conventional vertical urea reactor with heat removal and installed pervaporation membranes.

DETAILED DESCRIPTION OF THE INVENTION

Figure 1:
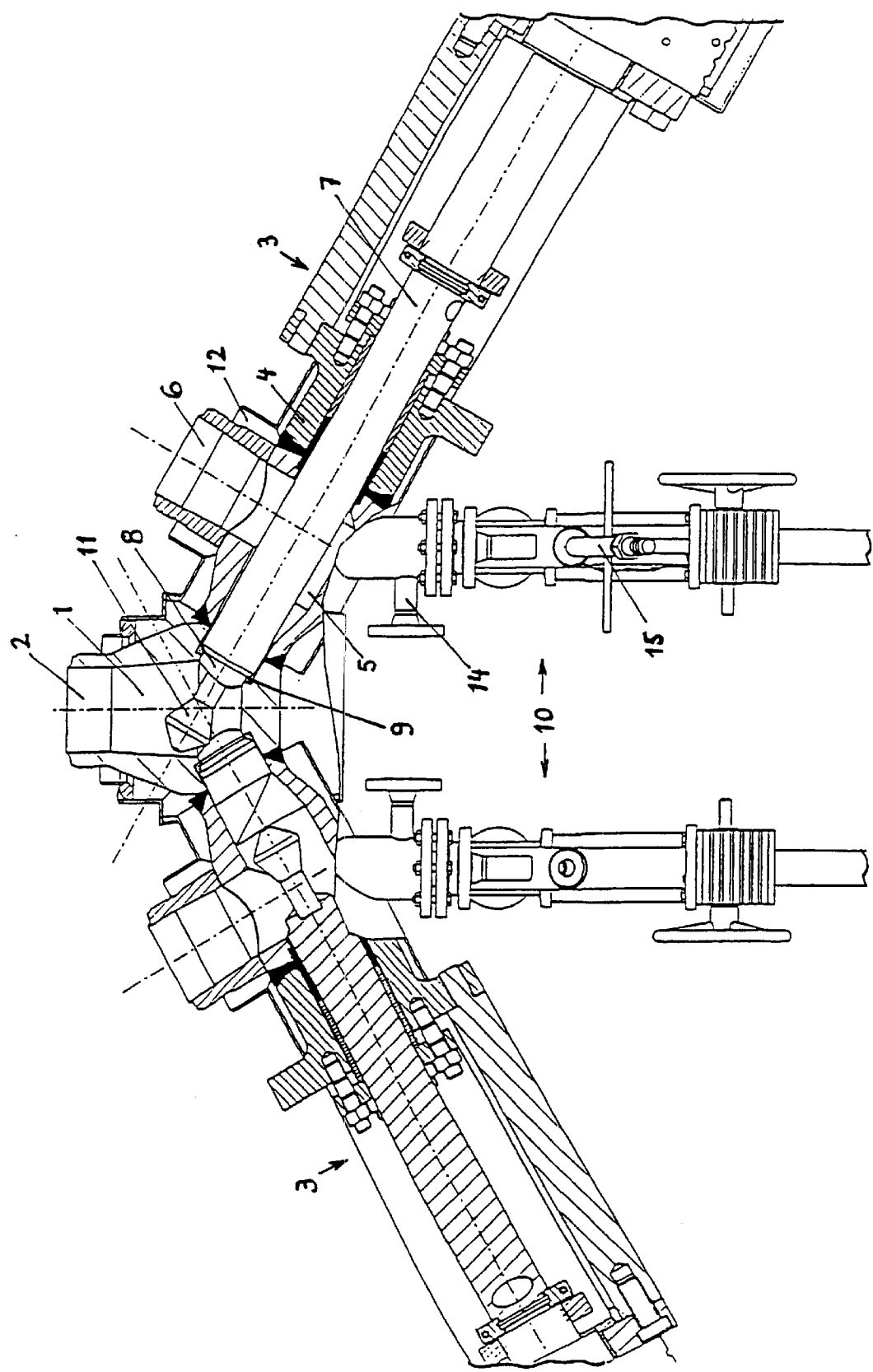
FIG. 1 shows a horizontal urea reactor with heat removal and installed pervaporation membranes.

FIG. 1 shows a high-pressure section of a urea plant with a horizontal reactor. In FIG. 1 (A) indicates a horizontal reactor with inter pervaporation membranes, condensation zone and heat exchanger, (B) indicates a stripping zone, (C) indicates a steam reservoir, (H) indicates a condenser and (D), (E), (F), (G) and (I) indicate (vacuum) pumps and compressors.

By means of pump (E) liquid ammonia is fed via line (1) and via a line (4) provided with openings to the condensation zone of the reactor. A carbamate solution that has been obtained elsewhere in the process, specifically by washing off-gases with an aqueous solution which has been obtained on evaporation of the urea solution, is drawn in via line (2). The ammonium carbamate solution is fed via line (3) to the reactor (A). A mixture containing ammonia and carbon dioxide is fed into the liquid via line (5) provided with openings. This gas mixture, supplied via line (15), has been obtained by subjecting the urea synthesis solution formed in the reactor to a stripping treatment in the stripping zone (B) wit the supply of heat and in counter-current to a stripping gas via line (13), for example carbon dioxide. In the embodiment shown, the pressures in rector (A) and the stripping zone (B) are virtually identical, for example 140 bar. The pressures and temperatures in the said zones can, however, also differ from one another. The reactor is furthermore provided with baffles, which divide the reactor into compartments.

The removal of water from the reactor takes place via the (ceramic) pervaporation membrane modules (19) which are positioned in the compartments between the baffles (in Figure five such modules are shown; this number can be higher or lower, depending on the size of thee rector), upstream of the last but one compartment, in which tapping is controlled by means of the reactor level. The positioning of these modules is above line (5) such that the gas comes thoroughly into contact with the liquid which is flowing ever the membranes and ensures good mixing. The water removed via the (ceramic) membranes is fed via a condenser (H) using a (vacuum) pump (I). The vapour, mainly consisting of water, is condensed in this condenser (H). The condensed steam from the condenser (21) and the vapour stream from the vacuum pump (22) are, for example, fed to a stripper in the effluent treatment plant. The effluent treatment plant for the urea process has not been drawn here.

The heat liberated in the reactor is removed with the aid of water, supplied via line (6), which is fed by means of pump (G) via (7) through the heat exchanger (8) mounted in the reactor (A) and which during this operation is converted into low-pressure steam. The steam formed is fed via line (9) into steam reservoir (C) and discharged from the latter via line (10) to installation, which is not shown, which uses low-pressure steam, for example the recirculation and/or evaporation section. Heat is supplied to the water-removing and heat-removing pervaporation membranes (19) by means of heat which is supplied by carbamate formation in the reactor feed and a targeted supply of condensing stripper gas via line (15) and correct dimensioning of distributor (5) to provide the correct distribution.

The inert gases, which additionally also contain ammonia and $CO_2$, are discharged from the reactor (A) via lie (14). $NH_3$ and $CO_2$ are removed from these gases in a known manner. The urea synthesis solution is fed from the reactor (A) via line (11) to the stripping zone (B). The stripped urea synthesis solution is discharged via line (12) and further processed in a known manner to give an aqueous urea solution and concentrated, after which the concentrated solution is optionally converted to solid urea.

FIG. 2 shows a conventional vertical urea reactor with a heat discharge and installed pervaporation membranes.

FIG. 2 shows the high-pressure section of a conventional urea process with a vertical reactor (A). The condensation step for the stripped carbamate stream (4) from the stripper (B) is shown in (C). The partially condensed stream from condenser (C) is fed into the bottom of the vertical reactor (A).

The overflow from reactor (A), which contains urea and unconverted carbamate, is subjected via (6), to the stripping treatment, resulting in a stripped stream (4) and a urea solution which is optionally converted to solid urea in a known manner.

The reactors described above can, for example be designed for the production of 1,500 m urea/day.

FIG. 1 shows the reactor (A) and stripper (B) and a few further pieces of equipment thereof, Via stream 21 20 tonnes/h water is discharged from reactor by means of the (vacuum) pump (I) and condenser (H) via the ceramic pervaporation elements 19 which have been installed between the various segments in the reactor.

Compared with known processes, inter alia the following advantages are achieved with the invention:

shift in the equilibrium towards the formation of urea, as a result of which a higher yield is obtained;

lower energy consumption, inter alia as a result of;
- 60% reduction in import of expensive medium-pressure steam
- no further export production of export low-pressure steam which is difficult to sell and yields virtually nothing
- 30% less evaporation is required in the urea evaporation step
- the load to the medium-pressure recycle is reduced by, 15%;

reduction in the dimensions of the equipment to be used. For instance, the reactor volume and the heat-exchange surface area can be reduced by 30%, the surface area of he stripper (B) can be reduced by 35% and the surface area of the carbamate condenser can be reduced by 50%.

What is claimed is:

1. Method for the preparation of urea from a reaction mixture in a reactor using ammonia and carbon dioxide as starting materials, which method comprises
    a) bringing the ammonia and carbon dioxide into contact in the reactor under conditions for the formation of ammonium carbamate; and
    b) dehydrating the ammonium carbamate thus formed to give urea and water, wherein the reaction mixture is brought into contact in the reactor with one side (reaction mixture side) of a water-selective membrane, the water formed during step b) being removed from the reaction mixture through said membrane to the other (discharge) side of the membrane, characterised in that the membrane is a pervaporation membrane and that a pressure difference is applied over the membrane with the higher pressure on the reaction mixture side, the water being removed as a vapour.

2. Method according to claim 1, wherein the discharge side of the membrane is connected to vacuum pump.

3. Method according to claim 1, wherein the water-selective membrane is a porous ceramic membrane.

4. Method according to claim 1, wherein the formation of urea is carried out in a cyclic process.

5. Method according to claim 1, wherein a reactor is used which is provided with one or more baffles, plates or trays which divide the reactor into two or more segments, each segment preferably being provided with a water-selective pervaporation membrane.

6. Method according to claim 1, wherein the design of the reactor, and in particular the positioning of the membranes, baffles, trays and walls in the reactor, is such that during operation the rising gas in the reactor gives rise to turbulent flow in the reactor, in particular at the surface of the one or more ceramic membranes.

7. Method according to claim 1, wherein the quantity of water that is removed from the reactor during operation is such that the abovementioned reaction steps a) and b) essentially can be carried out in a single reactor and the $CO_2$ feed gas can be fed directly to the reactor.

8. Method according to claim 1, wherein the temperature of the reactor, and in particular the heat required for the pervaporation, is essentially obtained/maintained by the carbamate reaction of feed components to the reactor and/or by condensation of the stripper gas supplied.

9. Method according to claim 2 wherein the discharge side of the membrane is also connected to a condenser to condense the vapors.

* * * * *